United States Patent [19]

Gerigk et al.

[11] Patent Number: 5,332,430
[45] Date of Patent: Jul. 26, 1994

[54] USE OF THIADIAZOLE COMPOUNDS AS AN ANTIFOULING ACTIVE INGREDIENT

[75] Inventors: Ursula Gerigk, Datteln; Dirk Ventur, Bochum, both of Fed. Rep. of Germany

[73] Assignee: Witco GmbH, Bergkamen, Fed. Rep. of Germany

[21] Appl. No.: 123,185

[22] Filed: Sep. 15, 1993

[30] Foreign Application Priority Data

Sep. 16, 1992 [DE] Fed. Rep. of Germany ....... 4230955

[51] Int. Cl.$^5$ .............................................. C09D 5/14
[52] U.S. Cl. ............................... 106/18.33; 106/18.35; 424/405; 427/384; 514/361; 514/363; 523/122; 548/128
[58] Field of Search ............... 106/18.33, 18.35; 514/363, 361; 548/128; 424/405; 427/384; 523/122

[56] References Cited

U.S. PATENT DOCUMENTS

| | | | |
|---|---|---|---|
| 4,209,522 | 6/1980 | Mixan et al. | 106/18.33 |
| 4,711,915 | 12/1987 | Doe, Jr. | 106/18.33 |
| 5,147,443 | 9/1992 | Diehr et al. | 106/18.33 |

FOREIGN PATENT DOCUMENTS

| | | | |
|---|---|---|---|
| 588046 | 12/1959 | Canada | 106/18.33 |
| 2142913 | 3/1972 | Fed. Rep. of Germany . | |
| 2439619 | 2/1975 | Fed. Rep. of Germany | 106/18.33 |
| 38-020133 | 10/1963 | Japan | 106/18.33 |
| 51-009705 | 1/1976 | Japan | 106/18.33 |
| 2-173165 | 7/1990 | Japan | 106/18.33 |
| 1356391 | 6/1974 | United Kingdom . | |

OTHER PUBLICATIONS

Green, T. W.,*Protective Groups in Organic Synthesis,* John Wiley & Sons, Inc., New York, pp. 288–334 (1981).

*Primary Examiner*—Anthony Green
*Attorney, Agent, or Firm*—Scully, Scott, Murphy & Presser

[57] ABSTRACT

The invention relates to thiadiazole compounds of the type

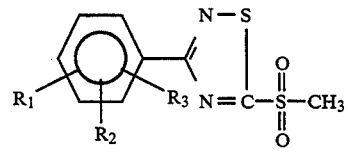

wherein $R_1$, $R_2$, $R_3$ are
  hydrogen
  alkyl groups having 1–4 carbon atoms
  substituted alkyl groups having 1–4 carbon atoms which are optionally substituted by halogen, carboxyl, hydroxyl, or nitro group
  alkoxy groups
  CN, $CF_3$, halogen or $NO_2$,
  COOR where R=H or alkyl groups having 1–4 carbon atoms which, as a consequence of their properties, are extremely effective biocides having broad antifouling properties and are suitable for biocidal finishing of surfaces in contact with sea water and for protecting these surfaces against colonization by marine organisms.

The compounds according to the invention are added to or copolymerized into the coatings which protect the surfaces, in 0.1–25% by weight, in particular 5–15%.

39 Claims, No Drawings

USE OF THIADIAZOLE COMPOUNDS AS AN ANTIFOULING ACTIVE INGREDIENT

The invention relates to the use of thiadiazole compounds as an antifouling active ingredients for protecting surfaces against marine organism growth.

Surfaces which are intended for underwater use, for example ships, boats, nets or offshore constructions, such as drilling platforms or pipelines, must be protected against marine organism growth, for example algae, seagrass, mussels, tube-worms, sponges, etc.

Fouling of the surfaces results in an increase in the upkeep and maintenance costs. In particular in the case of ships, fouling of the ship bottom increases the frictional resistance in water; this results in a significant reduction in speed or an increased consumption of fuel. In many cases, these surfaces are therefore protected by use of a suitable antifouling paint.

The antifouling paint usually comprises a polymeric binder, one or more biocides, which are leached out of the paint system in contact with water, and pigments.

Examples of polymeric binders employed are poly(meth)acrylates, polyesters, polyurethanes, epoxide compounds, chlorinated rubber, resins and other film-forming systems.

A wide range of different biocides are used in these antifouling paints. The most frequent are copper (I) salts, such as, for example, copper (I)-oxide, or organo-tin compounds, for example tributyltin methacrylate.

Since the use, in particular, of copper compounds is associated with technical disadvantages, there is a need for heavy-metal-free, alternative compounds for biocidal use in paint systems.

The preparation of novel diazole compounds of the general formula I

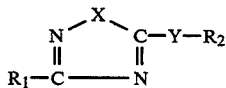

formula I and their use in pesticidal preparations and for controlling nematodes and fungi is described in DE-OS-2 142 913, the contents of which are incorporated by reference.

Surprisingly, it has now been found that certain thiadiazole compounds of the general formula II

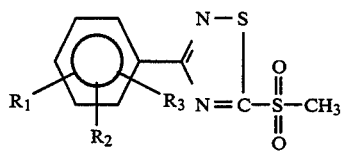

formula II where $R_1$, $R_2$, and $R_3$ are
hydrogen
alkyl groups having 1–4 carbon atoms
substituted alkyl groups having 1–4 carbon atoms which are optionally substituted by halogen, carboxyl, hydroxyl, or nitro group
alkoxy groups
CN, CF$_3$, halogen, or NO$_2$,
COOR where R is H or alkyl group having 1–4 carbon atoms have a very good action against marine organisms which participate in the fouling of surfaces in the marine sector.

The invention accordingly relates to the use of the compounds of the general formula II as an antifouling active ingredient.

Preference is given to compounds in which at least one of the groups $R_1$, $R_2$, and $R_3$ is hydrogen. It is also preferred that one of $R_1$, $R_2$, and $R_3$ is hydrogen, —CN, —NO$_2$, or halogen or alkyl (substituted or unsubstituted). In the case of substituted alkyl groups, halogen-, and NO$_2$-substituted groups are preferred. Furthermore, it is more preferred that one of $R_1$, $R_2$, and $R_3$ is hydrogen, CN, NO$_2$, or halogen. It is even more preferred that $R_1$ is hydrogen and $R_2$ is hydrogen, cyano, nitro, halogen, or unsubstituted or substituted alkyl. It is even more preferred that two of $R_1$, $R_2$, and $R_3$ are hydrogen.

As used herein, halogen refers to fluoro, iodo, chloro, or bromo. Chloro is the most preferred.

Alkoxy refers to a group having the substituent O-alkyl, wherein alkyl contains 1–4 carbon atoms.

The compounds of the present invention are prepared by art-recognized techniques. The starting materials are readily available or can easily be prepared by one skilled in the art. The methodology described in DE-OS-2 142 913 are also applicable here, and the contents thereof are incorporated by reference.

An exemplary example is as follows. A benzamidine of the formula

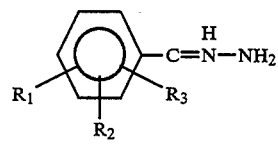

III wherein $R_1$, $R_2$, and $R_3$ are as defined herein, and more preferably a salt of benzamidine, such as benzamidium halide is refluxed with a methoxide salt such as alkali methoxide (e.g., sodium methoxide, potassium methoxide and the like), carbon disulfide and sulfur in methanol to form a thiadiazole compound of the formula

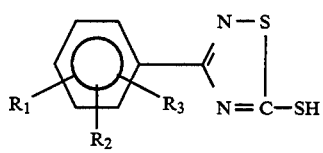

IV

This thiadiazole compound is heated with a base, (such as alkali carbonate, e.g., potassium carbonate) and methyl halide (e.g., methyl iodide) in an inert solvent, such as acetone and the like. Although the reaction can be effected at room temperature up to the refluxing temperature of the solvent, it is preferred that the reaction is heated under reflux. It is preferred that the reaction is refluxed for a few hours, usually about 2–5 hours, until the methyl thiadiazole derivative of the formula

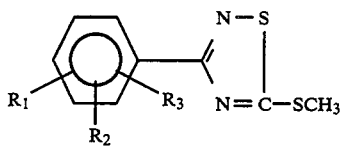

is formed. The product of the reflux is placed into water and the above product of Formula V is precipitated out. It can be used in the next step without further purification, but it is preferred that the compound of Formula V is purified, using techniques known to one skilled in the art, such as recrystallization and the like. If recrystallized, it is preferred that it is recrystallized from diethyl ether.

The methyl thiadiazole of Formula V is oxidized with an oxidizing agent, such as hydrogen peroxide, to form the corresponding methyl sulfonyl compound of Formula II.

Naturally, if any of the groups on $R_1$, $R_2$, and $R_3$ are reactive to the reaction conditions described hereinabove, they are protected by protecting groups. These protecting groups are known to one skilled in the art. Examples of such protecting groups are found in Green, *Protective Groups in Organic Synthesis*, John Wiley & Sons, Inc., New York, 1981, the contents of which are incorporated by reference.

The groups $R_1$, $R_2$, and $R_3$ may be added to the phenyl ring by aromatic substitution reactions known to one skilled in the art. For example, the alkyl group may be added to the aromatic ring by electrophilic alkylation reactions, such as Friedel Crafts Alkylation, known to one skilled in the art. The halogen may be added by electrophilic aromatic halogenation, while the nitro group may be added by nitration of the aromatic ring. The cyano derivative may be formed by nitrating the aromatic ring, reducing the nitro group with metal or hydrogen over palladium or platinum, converting the amino group to the diazonium ion by reacting the amino group with nitrous acid and reacting the diazonium salt with a metal cyanide, such as CuCN under Sandmeyer reaction conditions.

The carboxylic acid derivative can be prepared by several techniques known to one skilled in the art for example, by hydrolyzing the nitrile formed hereinabove, or by electrophilic formylation or alkylation of the aromatic ring followed by oxidation; or by nucleophilic substitution of aryl halide with CO by techniques known to one skilled in the art and the like. The esters are prepared from the carboxylic acids by techniques known to one skilled in the art; for example, the carboxylic acid is reacted with the alcohol in acid under esterification conditions.

The compounds are preferably used according to the invention in the form of preparations, such as solutions, emulsions, or dispersions, with or without binders or with solid carrier materials or diluents and optionally with the addition of wetting agents, adhesives, emulsifiers, and dispersants.

Typical diluents include for example, ketones such as acetone, methyl ethyl ketone (MEK) and the like; alcohol, such as ethanol, methanol, and the like; chlorinated hydrocarbons, such as chloroform, methylene chloride and the like. The diluents are preferably ketones, alcohols, and halogenated hydrocarbons, each containing 1-6 carbon atoms and more preferably 1-4 carbon atoms. The halogen in halogenated hydrocarbons are preferably chloro, and it is most preferred that the hydrocarbon contains 1-3 halogen atoms.

Typical wetting agents include fatty acids, polyphosphates, and the like.

Typical adhesives are silanes, metal aluminates, and the like.

Typical emulsifiers and dispersants are polyaminoamides, polycarboxylic acids, phosphatides, and the like.

The thiadiazole compounds are additionally used by mixing with polymers or by copolymerization. For example, the thiadiazole compounds of the present invention is mixed with a binder which is a polymer or a copolymer, such as poly-methylmethacrylate or copolymers of methacrylic acid and methylmethacrylate and/or butyl acrylate.

Examples of various types of formulations are described in DE-OS-2 142 913, the contents of which are incorporated by reference.

The carriers that are preferably used are those normally used in antifouling paints. These are known to one skilled in the art. The preferred carrier is an organic solvent.

Examples of suitable solvents are methanol, acetone, and aliphatic and aromatic hydrocarbons, such as hexane, toluene, xylene and the like.

As used herein, the active ingredient of the present invention comprises compounds of Formula II, as defined herein. It is preferred that the compounds of the present invention be present in the surface-protecting systems in a range between about 0.1 and about 25 percent by weight, preferably in the range of 0.1 to 20% by weight and more preferably in the range from about 5 to about 15% by weight.

In order to prepare antifouling paint systems, in accordance with the present invention, the compounds of Formula II and a polymeric binder system are mixed with pigments and optionally with other biocides in a suitable solvent.

Examples of polymeric binders are described hereinabove.

The pigments used herein are preferably sparingly water soluble and do not possess biocidal activity. Examples include titanium dioxide, iron oxide, and the like. The preferred pigments are water insoluble and delay rapid dissolution of the paint system.

The concentrations of the pigments can be up to 40 percent by weight of the total amount of pigment—but preferably less than 20 percent by weight.

The ratio between the polymeric binder and the total pigment concentration should be such that the pigment volume concentration is greater than 25% by weight in the dry film—it is preferably 35-50% by weight.

Examples of suitable solvents for the finished paints are aliphatic and aromatic hydrocarbons, such as, for example, toluene, xylene, and heptane; alcohols, such as butanol; ketones, such as methyl isobutyl ketone; or esters such as ethyl acetate or butyl acetate; petroleum hydrocarbon fractions, such as, for example, ligroin or benzine, or alternatively water, dimethylformamide or mixtures of the above solvents with one another, and the like. In addition, the solvents referred to hereinabove, such as methanol, acetone and hexane, can also be used.

The paint systems may furthermore contain a plasticizer, such as, for example, diisoctyl phthalate, tributyl phosphate, polyvinyl ethyl ether or a substituted sulfonamide, such as, for example, N-ethyl-p-toluenesulfonamide, and other auxiliaries, dispersants, antisettling agents, fillers, accelerators, retardants, and colorants or siccatives such as, for example, lime, Bentone, cobalt naphthenate or blue pigments.

The auxiliaries, dispersants, antisetting agents, fillers, accelerators, retardants and colorants are those that are commonly used. Examples of auxiliaries include stabilizers like casein or anti-foam agents, such as organosilicon compounds and the like.

Common dispersants are polycarboxylic acids, such as polymethacrylic acid, polyacrylic acid and the like.

Antisettling agents include montmorillonite earths, like bentonite, aerosil and the like.

Fillers include silicates, carbonates, like silicium dioxide, talc, kaolin, chalk and the like.

Examples of accelerators include vinyl polymers, like polyvinyl methylether, polyvinyl pyrrolidone, polyvinyl ethers, polyvinyl alcohols, and the like.

Retardants include chloroparaffins, naphthalenes, diphenylethers, and the like.

Colorants include pigments like titanium dioxide, carbon black, dyes like organic soluble colorants, such as ultramarine blue, and the like.

In addition, the composition of the present invention may contain a second compound containing biocidal activity, such as, for example,
2,4,5,6-tetrachloroisophthalonitrile,
2-methylthio-4-tert-butylamino-6-cyclopropylamino-s-triazine,
2-thiocyanomethylthiobenzothiazole,
3-(3,4-dichlorophenyl)-1,1-dimethylurea,
3-iodo-2-propynyl butylcarbamate,
dibromosuccinate,
diphenylamine,
isothiazolones,
zinc or manganese ethylenebisdithiocarbamates,
zinc pyrithione, and the like.

When the composition contains the thiadiazole compounds and the biocide, it is preferred that the thiadiazole compound be present in a range between about 0.1 and about 25% by weight, more preferably in the range of about 0.1 to about 20% by weight, and most preferably in the range of about 5 to about 15% by weight. When present, the cobiocide is present in concentration from but not including 0% to about 20% by weight. For example, the second biocide may be present from about 0.1% to about 20% by weight. It is more preferred that the second biocide be present in up to about 10% by weight.

PREPARATION EXAMPLES

EXAMPLE I

Synthesis of
5-Methylsulfonyl-3-phenyl-1,2,4-thiadiazole 75 g of benzamidinium chloride, 257 g of sodium methoxide (30% in methanol), 92 g of carbon disulfide, 19 g of sulfur and 450 g of methanol are refluxed for 6 hours. The excess carbon disulfide is removed by distillation via a distillation bridge, and the methanol is stripped off in a rotary evaporator. The residue is dissolved in hot water and filtered. The filtrate is acidified to pH 3 by means of hydrochloric acid, and the precipitated product is filtered off, taken up in potassium carbonate solution, filtered and re-precipitated by means of hydrochloric acid.

52 g of the thiadiazole compound 5-thio-3-phenyl-1,2,4-thiadiazole, 18.5 g of potassium carbonate, 54 g of methyl iodide and 270 ml of acetone are refluxed for 3 hours and stirred into 1.5 l of water, and the white precipitate is subsequently filtered off. The precipitate is recrystallized from ethyl ether.

20 g of 5-methylthio-3-phenyl-1,2,4-thiadiazole are dissolved in 250 ml of acetic acid, and 50 ml of 30% hydrogen peroxide solution are added. After 72 hours, the precipitate of 5-methylsulfonyl-3-phenyl-1,2,4-thiadiazole is filtered off and washed with water and hexane.

EXAMPLE II

Synthesis of
5-Methylsulfonyl-3-p-chlorophenyl-1,2,4-thiadiazole 90.2 g of p-chlorobenzamidinium chloride, 257 g of sodium methoxide (30% in methanol), 92 g of carbon disulfide, 19 g of sulfur and 450 g of methanol are refluxed for 7 hours. The further work-up is carried out analogously to the first example.

65 g of the thiadiazole compound 5-thio-3-p-chlorophenyl-1,2,4-thiadiazole, 19.2 g of potassium carbonate, 56.1 g of methyl iodide and 280 ml of acetone are refluxed for 4 hours and stirred into 1.6 l of water, and the white precipitate is subsequently filtered off. The precipitate is recrystallized from diethyl ether.

25 g of 5-methylthio-3-p-chlorophenyl-1,2,4-thiadiazole are dissolved in 260 ml of acetic acid and 52 ml of 30% hydrogen peroxide solution are added. After 72 hours, the precipitate of 5-methylsulfonyl-3-p-chlorophenyl-1,2,4-thiadiazole is filtered off and washed with water and hexane.

EXAMPLE III

Synthesis of
5-Methylsulfonyl-3-p-nitrophenyl-1,2,4-thiadiazole 94.8 of p-nitrobenzamidinium chloride, 257 g of sodium methoxide (30% in methanol), 92 g of carbon disulfide, 19 g of sulfur and 450 g of methanol are refluxed for 7 hours. The further work-up is carried out analogously to the first example.

63.5 g of the thiadiazole compound 5-thio-3-p-nitrophenyl-1,2,4-thiadiazole, 17.9 g of potassium carbonate, 52.2 g of methyl iodide and 260 ml of acetone are refluxed for 4 hours and stirred into 1.4 l of water, and the white precipitate is subsequently filtered off. The precipitate is recrystallized from diethyl ether.

19 g of 5-methylthio-3-p-nitrophenyl-1,2,4-thiadiazole are dissolved in 237.5 ml of acetic acid and 47.5 ml of 30% hydrogen peroxide solution are added. After 72 hours, the precipitate of 5-methylsulfonyl-3-p-nitrophenyl-1,2,4-thiadiazole is filtered off and washed with water and hexane.

EXAMPLE IV

Synthesis of
5-Methylsulfonyl-3-p-tolyl-1,2,4-thiadiazole 81.4 g of p-methylbenzamidinium chloride, 257 g of sodium methoxide (30% in methanol), 92 g of carbon disulfide, 19 g of sulfur and 450 g of methanol are refluxed for 5.5 hours. The further work-up is carried out analogously to the first example.

58.3 of the thiadiazole compound 5-thio-3-p-tolyl-1,2,4-thiadiazole, 19.1 g of potassium carbonate, 55.8 g of methyl iodide and 280 ml of acetone are refluxed for 4 hours and stirred into 1.55 l of water, and the white precipitate is subsequently filtered off. The precipitate is recrystallized from diethyl ether.

21.7 g of 5-methylthio-3-p-tolyl-1,2,4-thiadiazole are dissolved in 250 ml of acetic acid and 50 ml of 30% hydrogen peroxide solution are added. After 72 hours, the precipitate of 5-methylsulfonyl-3-p-tolyl-1,2,4-thiadiazole is filtered off and washed with water and hexane.

EXAMPLE V

Synthesis of 5-Methylsulfonyl-3-(2,4-dichloro)phenyl-1,2,4-thiadiazole 105.2 g of 2,4-dichlorobenzamidinium chloride, 257 g of sodium methoxide (30% in methanol), 92 g of carbon disulfide, 19 g of sulfur and 450 g of methanol are refluxed for 7 hours. The further work-up is carried out analogously to the first example.

73 g of the thiadiazole compound 5-thio-3-(2,4-dichloro)phenyl-1,2,4-thiadiazole, 18.5 g of potassium carbonate, 54 g of methyl iodide and 270 ml of acetone are refluxed for 4 hours and stirred into 1.5 l of water, and the white precipitate is subsequently filtered off. The precipitate is recrystallized from diethyl ether.

25 g of 5-methylthio-3-p-(2,4-dichloro)phenyl-1,2,4-thiadiazole are dissolved in 220 ml of acetic acid and 44.6 ml of 30% hydrogen peroxide solution are added. After 72 hours, the precipitate of 5-methylsulfonyl-3-p-(2,4-dichloro)phenyl-1,2,4-thiadiazole is filtered off and washed with water and hexane.

FORMULATION EXAMPLES

Formulation Examples 1-3

Various amounts of methacryl acid, methyl methacrylate, and butyl acrylate (see Table 1) were copolymerized for 4 hours at 70°–80° C. in n-butanol under nitrogen by means of $\alpha,\alpha'$-azoisobutyronitrile or dibenzoyl peroxide. The table below shows some illustrative examples:

TABLE 1

|  | METHACRYLIC ACID [g] | METHYL METHACRYLATE [g] | BUTYL ACRYLTE [g] |
|---|---|---|---|
| Polymer a | 39.3 | 138.6 | 122.1 |
| Polymer b | 68.7 | 107.7 | 123.6 |
| Polymer c | 74.1 | 101.7 | 124.2 |

122 g of the above polymer a, b, or c were ground for one hour with 56 g of Bentone 38 (gelling agent based on montmorillonite earth, 6% in xylene, Titangesellschaft), 10.4 g of talc, 4.6 g of titanium dioxide RN 57 (Bayer), 0.8 g of Ultramarine Blue L 6294 (colored pigments, BASF) and 12.3 g of 50-methylsulfonyl-3-phenyl-1,2,4-thiadiazole and 40 g of xylene.

Formulation Example 4

An epoxy resin-based antifouling paint was prepared by mixing the two components A: EUREPOX ® 7001 (trade mark of Witco)[1] (17.2% by weight), titanium dioxide (38.6% by weight), tributyl phosphate (2.6% by weight), 5-methylsulfonyl-3-phenyl-1,2,4-thiadiazole (11.6% by weight), xylene (24.0% by weight), n-butanol (6.0% by weight) and component B: EUREDUR ® 423 (trade mark of Witco)[2] (14.5% by weight).
[1]EUREPOX ® 7001=solid epoxy resin based on bisphenol-A having an epoxide value (DIN 53188) 0.195–0.225.
[2]EUREDUR ® 423=polyaminoamide/epoxy resin adduct in xylene:n-BuOH 4:1 based on dimeric fatty acid, triethylene tetramine and an epoxy resin based on bisphenol A having an amine number of 125–140.

Formulation Example 5

A chlorinated rubber-based antifouling paint was prepared by mixing and grinding 14.3% by weight of Pergut S 20 (medium-viscosity chlorinated rubber from Bayer AG), 7.1% by weight of Witachlor 544 (chlorinated paraffin having a chlorine content of 44%, Dynamit Nobel AG), 5-methylsulfonyl-3-phenyl-1,2,4-thiadiazole (12.9% by weight), titanium dioxide (23.6% by weight), copper thiocyanate 6.4% by weight and xylene (35.7% by weight).

Formulation Example 6

A vinyl resin-based antifouling paint was prepared by blending and subsequently grinding 9.8% by weight of vinylite VYHH, colophony (9.8% by weight), 5-methylsulfonyl-3-phenyl-1,2,4-thiadiazole (12.2% by weight), a 10% solution of Bentone 27 in xylene (10.1% by weight), xylene (7.8% by weight), methyl isobutyl ketone (30.1% by weight) and titanium dioxide (20.2% by weight).

Formulation Examples 7-9

122 g of the above polymer a, b, or c described in Formulation Example 1 were ground for one hour with 56 g of Bentone 38, 10.4 g of talc, 4.6 g of titanium dioxide, 0.8 g of Ultramarine Blue L 6294 and 12.3 g of 5-methylsulfonyl-3-p-chlorophenyl-1,2,4-thiadiazole and 40 g of xylene.

Formulation Example 10

An epoxy resin-based antifouling paint was prepared by mixing the two components. Component A: Eurepox ® 7001 (17.2% by weight), titanium dioxide (38.6% by weight), tributyl phosphate (2.6% by weight), 5-methylsulfonyl-3-p-nitrophenyl-1,2,4-thiadiazole (11.6% by weight), xylene (24.0% by weight), n-butanol (6.0% by weight) and component B: EUREDUR ® 423 (14.5% by weight).

Formulation Example 11

A chlorinated rubber-based antifouling paint was prepared by mixing and grinding 14.3% by weight of Pergut S 20, 7.1% by weight of Witachlor 544, 5-methylsulfonyl-3-p-tolyl-1,2,4-thiadiazole (12.9% by weight), titanium dioxide (23.6% by weight), copper thiocyanate 6.4% by weight and xylene (35.7% by weight).

Formulation Example 12

A vinyl resin-based antifouling paint was prepared by blending and subsequently grinding 9.8% by weight of Vinylite VYHH, colophony (9.8% by weight), 5-methylsulfonyl-3-(2,4-dichloro)phenyl-1,2,4-thiadiazole (12.2% by weight), a 10% solution of Bentone 27 in xylene (10.1% by weight), xylene (7.8% by weight), methyl isobutyl ketone (30.1% by weight) and titanium dioxide (20.2% by weight).

Formulation Example 13

61 g of a copolymer (13 parts of methacrylic acid, 47 parts of methyl methacrylate and 40 parts of butyl acrylate) were mixed with 28 g of Bentone 38, 5.2 g of talc, 2.3 g of titanium dioxide, 0.4 g of blue pigment, 6.2 g of zinc oxide and 20 g of xylene, and the mixture was ground for two hours.

Formulation Example 14

61 g of a copolymer (25 parts of methacrylic acid, 35 parts of methyl methacrylate and 40 parts of butyl acrylate) were mixed with 28 g of Bentone 38 (6% in xylene), 5.2 g of talc, 2.3 g of titanium dioxide, 0.4 g of Ultramarine Blue L 6294, 6.2 g of zinc oxide and 20 g of xylene, and the mixture was ground for one hour.

Formulation Example 15

Untreated PVC sheet

The effectiveness of the thiadiazole types according to the invention against marine organisms was determined by immersion tests both in the Mediterranean and in the North seas.

For this purpose, test sheets of polyvinyl chloride (10×15×1.4 cm) were provided with antifouling paints. This was carried out by the following procedure.

The PVC sheets were degreased and subsequently coated twice with the antifouling paint and dried for 48 hours. The dry film thickness is then 100–150 μm. The PVC sheets are clamped in a plastic frame and immersed for a period of 15 months. The table below clearly shows that test sheets with the compounds according to the invention were free from animal or vegetable fouling in this period.

The test sheets without the compounds according to the invention exhibited considerable fouling by algae, barnacles, and mussels.

Formulation Examples 13, 14, and 15 served as a control in the immersion tests.

TABLE 2

| Formulation Example No. | 6 months | 12 months | 15 months |
| --- | --- | --- | --- |
| Example 1 | 0 | 0 | 0 |
| Example 2 | 0 | 0 | 0 |
| Example 3 | 0 | 0 | 0 |
| Example 4 | 0 | 0–1 | 1 |
| Example 5 | 0 | 0 | 0 |
| Example 6 | 0 | 0 | 0–1 |
| Example 7 | 0 | 0 | 0–1 |
| Example 8 | 0 | 0 | 0–1 |
| Example 9 | 0 | 0 | 0–1 |
| Example 10 | 0 | 1 | 1–2 |
| Example 11 | 0 | 1 | 1–2 |
| Example 12 | 0 | 0–1 | 1 |
| Example 13 | 5 | 10 | 10 |
| Example 14 | 7 | 10 | 10 |
| Example 15 | 10 | 10 | 10 |

0 = no fouling
5 = 50% fouling
10 = complete fouling

What is claimed is:

1. An antifouling composition comprising an antifouling effective amount of a biocide having the formula

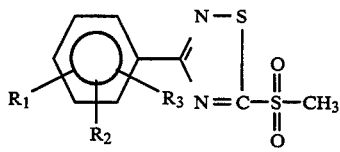

and a biocidal carrier therefor
wherein
$R_1$, $R_2$ and $R_3$ are independently hydrogen, CN, CF$_3$ halogen, NO$_2$, COOR, or alkyl having 1–4 carbon atoms which is unsubstituted or substituted with halogen, carboxy, hydroxy, or nitro, or $R_1$, $R_2$ and $R_3$ are alkoxy having 1–4 carbon atoms, and R is hydrogen or alkyl groups having 1–4 carbon atoms.

2. The antifouling composition according to claim 1 wherein at least one of $R_1$, $R_2$, and $R_3$ is hydrogen.

3. The antifouling composition according to claim 1 wherein at least one of $R_1$, $R_2$, and $R_3$ is hydrogen, CN, NO$_2$, halogen or unsubstituted or substituted alkyl.

4. The antifouling composition according to claim 3 wherein substituted alkyl is alkyl substituted with halogen or NO$_2$.

5. The antifouling composition according to claim 1 wherein $R_1$ is hydrogen and $R_2$ is hydrogen, cyano, NO$_2$, halogen, or unsubstituted or substituted alkyl.

6. The antifouling composition according to claim 1 wherein the biocide is 5-methylsulfonyl-3-phenyl-1,2,4-thiadiazole.

7. The antifouling composition according to claim 1 wherein the biocide is 5-methylsulfonyl-3-p-chlorophenyl-1,2,4-thiadiazole, 5-methylsulfonyl-3-p-nitrophenyl-1,2,4-thiadiazole, 5-methylsulfonyl-3-p-tolyl-1,2,4-thiadiazole, or 5,-methylsulfonyl-3-(2,4-dichloro)phenyl-1,2,4-thiadiazole.

8. The antifouling composition according to claim 1 in which the biocide is present in concentrations ranging from 0.1 to 25% by weight.

9. The antifouling composition according to claim 8 wherein the biocide is present in concentrations ranging from 5 to 15% by weight.

10. The antifouling composition according to claim 1 wherein a polymeric binder is additionally present.

11. The antifouling composition according to claim 1 additionally comprising a second biocide in a concentration of up to about 20% by weight.

12. The antifouling composition according to claim 11 wherein the second biocide agent is 2,4,5,6-tetrachloroisophthalonitrile, 2-methylthio-4-tert-butylamino-6-cyclopropylamino-s-triazine, 2-thiocyanomethylthiobenzothiazole, 3-(3,4-dichlorophenyl)-1,1-dimethylurea, 3-iodo-2-propynylbutylcarbamate, dibromosuccinate, diphenylamine, isothiazolone, zinc or manganese ethylenebisdithiocarbamate or zinc pyrithione.

13. The antifouling paint comprising a biocidal effective amount of a biocide having the formula

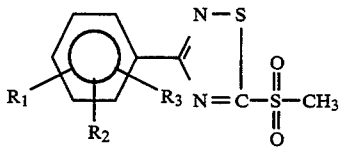

in association with a paint pigment, a polymeric binder, and a carrier, wherein
$R_1$, $R_2$ and $R_3$ are independently hydrogen, CN, CF$_3$ halogen, NO$_2$, COOR, or alkyl having 1–4 carbon atoms which is unsubstituted or substituted with halogen, carboxy, hydroxy, or nitro, or $R_1$, $R_2$ and $R_3$ are alkoxy having 1–4 carbon atoms, and R is hydrogen or alkyl groups having 1–4 carbon atoms.

14. The paint according to claim 13 wherein at least one of $R_1$, $R_1$, and $R_3$ is hydrogen.

15. The paint according to claim 13 wherein at least one of $R_1$, $R_2$, and $R_3$ is hydrogen, CN, $NO_2$, halogen, or unsubstituted or substituted alkyl.

16. The paint according to claim 15 wherein substituted alkyl is alkyl substituted with halogen or $NO_2$.

17. The paint according to claim 13 wherein $R_1$ is hydrogen and $R_2$ is hydrogen, cyano, $NO_2$, halogen, or unsubstituted or substituted alkyl.

18. The paint according to claim 13 wherein the biocide is 5-methylsulfonyl-3-phenyl-1,2,4-thiadiazole.

19. The paint according to claim 13 wherein the biocide is 5-methylsulfonyl-3-p-chlorophenyl-1,2,4-thiadiazole, 5-methylsulfonyl-3-p-nitro-phenyl-1,2,4-thiadiazole, 5-methylsulfonyl-3-p-tolyl-1,2,4-thiadiazole, or 5-methylsulfonyl-3-(2,4-dichloro)phenyl-1,2,4-thiadiazole.

20. The paint according to claim 13 wherein the biocide is present in concentrations ranging from 0.1 to 25% by weight.

21. The paint according to claim 13 wherein the biocide is present in concentrations ranging from 5 to 15% by weight.

22. The paint according to claim 13 which additionally comprises a second biocidal agent in a concentration of up to about 20% by weight.

23. The paint according to claim 22 wherein the second biocidal agent is 2,4,5,6-tetrachloroisophthalonitrile, 2-methylthio-4-tert-butylamino-5-cyclopropylamino-s-triazine, 2-thiocyanomethylthiobenzothiazole, 3-(3,4-dichlorophenyl)-1,1-dimethylurea, 3-iodo-2-propynylbutylcarbamate, dibromosuccinate, diphenylamine, isothiazolone, zinc or manganese ethylenebisdithiocarbamate, or zinc pyrithione.

24. A method for protecting a surface in contact with sea water against marine organism growth comprising applying to said surface a biocidal effective amount of a biocide of the formula:

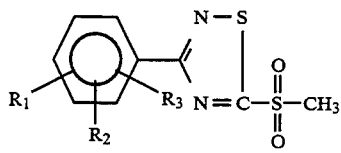

wherein
$R_1$, $R_2$ and $R_3$ are independently hydrogen, CN, $CF_3$, halogen, $NO_2$, COOR, or alkyl having 1-4 carbon atoms which is unsubstituted or substituted with halogen, carboxy, hydroxy, or nitro, or $R_1$, $R_2$ and $R_3$ are alkoxy having 1-4 carbon atoms, and R is hydrogen or alkyl groups having 1-4 carbon atoms.

25. The method according to claim 24 wherein at least one of $R_1$, $R_2$, and $R_3$ is hydrogen.

26. The method according to claim 24 wherein at least one of $R_1$, $R_2$, and $R_3$, is hydrogen, CN, $NO_2$, halogen, or unsubstituted or substituted alkyl.

27. The method according to claim 26 wherein substituted alkyl is alkyl substituted with halogen or $NO_2$.

28. The method according to claim 24 wherein $R_1$ is hydrogen and $R_2$ is hydrogen, cyano, $NO_2$, halogen, or unsubstituted or substituted alkyl.

29. The method according to claim 24 wherein the compound is 5-methylsulfonyl-3-phenyl-1,2,4-thiadiazole.

30. The method according to claim 24 wherein the compound is 5-methylsulfonyl-3-p-chlorophenyl-1,2,4-thiadiazole, 5-methylsulfonyl-3-p-nitro-phenyl-1,2,4-thiadiazole, 5-methylsulfonyl-3-p-tolyl-1,2,4-thiadiazole, or 5-methylsulfonyl-3-(2,4-dichloro)phenyl-1,2,4-thiadiazole.

31. The method according to claim 24 wherein said compound is in association with a pigment, a polymeric binder and a carrier.

32. The method according to claim 24 wherein said compound is in association with a second biocide in a concentration of up to about 20% by weight.

33. The method according to claim 32 wherein the second biocide is 2,4,5,6-tetrachlorisophthalonitrile, 2-methylthio-4-tert-butylamino-6-cyclopropylamino-s-triazine, 2-thiocyanomethylthiobenzothiazole, 3-(3,4-dichlorophenyl)-1,1-dimethylurea, 3-iodo-2-propynyl butylcarbamate, dibromosuccinate, diphenylamine, isothiazolone, zinc or manganese ethylenebisdithiocarbamate, or zinc pyrithione.

34. The method according to claim 32 wherein the second biocide is present in concentrations greater than 0% and up to about 20% by weight.

35. The method according to claim 34 wherein the second biocide is present in up to 10% by weight.

36. The antifouling composition according to claim 1 wherein the second biocide is present in concentrations greater than 0% and up to about 20% by weight.

37. The antifouling composition according to claim 36 wherein the second biocide is present in up to by weight.

38. The paint according to claim 22 wherein the second biocide is present in concentrations greater than and up to about 20% by weight.

39. The paint according to claim 38 wherein the second biocide is present in up to 10% by weight.

* * * * *

UNITED STATES PATENT AND TRADEMARK OFFICE
CERTIFICATE OF CORRECTION

PATENT NO. : 5,332,430
DATED : July 26, 1994
INVENTOR(S) : Ursula Gerigk, et al.

It is certified that error appears in the above-indentified patent and that said Letters Patent is hereby corrected as shown below:

Column 1, line 61: "carbon atoms" should read --carbon atoms--

Column 10, line 68, Claim 14: "$R_1$" (2nd occurrence) should read --$R_2$--.

Column 12, line 45, Claim 37: "to by" should read --to 10% by--

Column 12, line 48, Claim 38: "than and" should read --than 0% and--

Signed and Sealed this

Twenty-second Day of November, 1994

Attest:

BRUCE LEHMAN

*Attesting Officer*  *Commissioner of Patents and Trademarks*